United States Patent [19]

Yoshida et al.

[11] Patent Number: 4,894,327

[45] Date of Patent: Jan. 16, 1990

[54] ANTI-HUMAN MESOTHELIAL CELL MONOCLONAL ANTIBODY

[75] Inventors: Hajime Yoshida, Sagamihara, Japan; Nobuo Hanai, Mercer Island, Wash.

[73] Assignee: Kyowa Hakko Kogyo Co., Ltd., Tokyo, Japan

[21] Appl. No.: 112,149

[22] Filed: Oct. 26, 1987

[30] Foreign Application Priority Data

Oct. 28, 1986 [JP] Japan .................................. 61-256142

[51] Int. Cl.$^4$ ................. G01N 33/577; G01N 33/574; C12N 5/00; C12N 15/00
[52] U.S. Cl. .................................. 435/7; 435/240.27; 435/70.21; 435/172.2; 436/501; 436/512; 424/3; 424/7.1
[58] Field of Search ............ 435/7, 240.27, 68, 172.2; 436/501, 512; 424/3, 7.1; 530/387

[56] References Cited

U.S. PATENT DOCUMENTS 4,792,521 12/1988 Shochat .................................. 435/7

OTHER PUBLICATIONS

Mason, et al., in Annals of the N.Y. Academy Science, 420, pp. 127–133, 1983.
Cordell, et al., British J. Cancer 52(3), pp. 347–354, 1985.

*Primary Examiner*—Christine M. Nucker
*Assistant Examiner*—Karen J. Krupen
*Attorney, Agent, or Firm*—Antonelli, Terry & Wands

[57] ABSTRACT

A monoclonal antibody is disclosed capable of specifically reacting with the human mesothelial cell but not with other normal cells and human tumor cells, and therefore applicable in diagnosis of cancers.

3 Claims, No Drawings

ANTI-HUMAN MESOTHELIAL CELL MONOCLONAL ANTIBODY

BACKGROUND OF THE INVENTION

The present invention relates to a monoclonal antibody capable of specifically reacting with the human mesothelial cell and to a method of producing the monoclonal antibody. The present invention is useful in diagnosis of cancers such as cytological diagnosis of expectoration for lung cancer, cytological diagnosis of pleural effusion for lung cancer and cytological diagnosis of ascitic fluid for various abdominal cancers.

It is known that in lung cancer, cancer cells desquamate into sputum and/or pleural effusion, and that in various abdominal cancers, cancer cells desquamate into ascitic fluid. Therefore, it is important in diagnosis of cancer to detect cancer cells desquamating into sputum and/or pleural effusion, or ascitic fluid. Diagnosis and differentiation of cancer cells are generally carried out by pathologists. Sputum, pleural effusion and ascitic fluid contain many kinds of normal cells, and above all it is difficult to distinguish cancer cells from mesothelial cells and macrophages.

Recently, many monoclonal antibodies having specificity for cancer cells have been produced by hybridoma technique, and application of the monoclonal antibodies to cytodiagnosis have been made. Since some of the monoclonal antibodies react with macrophages and/or mesothelial cells or some of them react only with particular cancer cells, it is not easy to carry out cytodiagnosis of cancer by use of the monoclonal antibodies. Especially, it is difficult for even a pathologist to distinguish cancer cells from mesothelial cells.

Accordingly, a monoclonal antibody which specifically reacts with the mesothelial cell but not with cancer cells, if available, would be useful in the cytodiagnosis of cancer. No monoclonal antibodies and antisera being capable of specifically reacting with the mesothelial cell have been know so far.

The present inventors have first produced hybridomas between spleen cells of a mouse immunized with human mesothelial cells and murine myeloma cells and selected a hybridoma producing a monoclonal antibody which is capable of specifically reacting with human mesothelial cells but not with various human cancer cells. Further, the present inventors have made cytological diagnosis of expectoration, pleural effusion and ascitic fluid from patients with cancer using the monoclonal antibody of the present invention has a great significance in clinical pathology, and have now completed the present invention.

SUMMARY OF THE INVENTION

The present invention provides a monoclonal antibody of the IgG class capable of specifically reacting with human mesothelial cells but not with other normal human cells and human tumor cells.

DESCRIPTION OF THE INVENTION

The monoclonal antibody according to the present invention is obtained by fusing spleen cells of a mouse immunized with human mesothelial cells, with murine myeloma cells to prepare hybridomas, selecting from among the resulting hybridomas a hybridoma clone producing the required monoclonal antibody, and cultivating the selected hybridoma in a suitable culture medium or intraperitoneally administering the selected hybridoma to a mouse thereby to cause hybridoma cell propagation in the ascitic fluid in the mouse, followed by separation of the product antibody from the culture medium or the ascitic fluid as the case may be.

A method of producing the monoclonal antibodies according to the invention is described in detail below.

(1) IMMUNIZATION OF ANIMAL AND PREPARATION OF ANTIBODYPRODUCING CELLS

Mice between 3–10 weeks of age, preferably 8-week-old mice, are immunized with human mesothelial cells, to cause such mice to prepare antibody-producing cells in the spleen, lymph node and peripheral blood. The immunization is performed generally by administering human mesothelial cells ($5 \times 10^5$ to $5 \times 10^6$ cells per animal), together with an appropriate adjuvant (e.g. Freund's complete adjuvant, or aluminum hydroxide gel plus B. pertussis vaccine) to the mice subcutaneously, intravenously or intraperitoneally. Thereafter, the same antigen administration is repeated 2 to 5 times at 1 to 2 week intervals. Three to seven days after each immunization, the blood is sampled from the eyeground venous plexus and the serum of each sample is tested to determine whether it reacts with human mesothelial cells by the immunocytochemical staining given hereinafter.

Immunocytochemical staining:

A mesothelial cell suspension ($1 \times 10^7$ cells/ml) in PBS comprising 1.83 g of disodium phosphate, 0.21 g of monopotassium phosphate and 7.65 g of sodium chloride in 1 l of distilled water (pH 7.2) is distributed into the wells of a 12-well micro-titer slide glass (Flow Laboratories, CAT No. 60-412-05) coated with egg white albumin in an amount of 5 μl per well and dried over cooled air for 5 to 10 minutes.

Then, acetone cooled at $-20°$ to $-30°$ C. is added to each well and the slide glass is allowed to stand for 10 minutes. After drying for 2 to 3 minutes, endogenous peroxidase is inactivated by immersion in 3% hydrogen peroxide in methanol solution for 30 minutes. After washing well with PBS, 20 μl of antiserum or monoclonal antibody solution (1 to 20 μg/ml) is distributed into each well as the first antibody, and the slide glass is allowed to stand for 30 minutes to 2 hours at room temperature and washed well with PBS. Then, 20 μl of a biotin-labeled rabbit anti-mouse immunoglobulin (10 μg/ml) is distributed into each well as the second antibody, and the glass is allowed to stand at room temperature for 30 minutes and then washed well with PBS. Avidin-biotin-perioxidase complex (ABC reagent, product of Vector) is added to the wells, and the glass is allowed to stand at room temperature for 30 minutes and then washed well with PBS. Color is developed by the addition of diaminobenzidine as the substrate solution for peroxidase, and the glass is observed with a microscope.

The procedure subsequent to ABC reagent is made by the method recommended by Vector. When the target cell is various tumor cells or normal cells instead of mesothelial cells, the immunocytochemical staining is conducted in the same manner except for changing a cell fixed on a slide glass as the first step. In preparation for cell fusion, human mesothelial cells are intraperitoneally administered to the immunized mice in a dose of $5 \times 10^5$ to $5 \times 10^6$ cells per animal 3 to 4 days prior to the fusion treatment. The spleens are then extirpated and the spleen cells are prepared for fusion.

That is, the spleen is cut into fragments in MEM (product of Nissui Pharmaceutical), loosened up with forceps, and centrifuged at 1,200 rpm for 5 minutes. The supernatant is discarded, and the sediment are deprived of erythrocytes by treatment with Tris-ammonium chloride buffer (pH 7.65) for 1–2 minutes, washed three times with MEM, and used as the spleen cells for fusion.

Mesothelial cells are obtained from intine of thorax and of abdominal cavity on autopsies. Cells are collected from the surface of the intine and washed with PBS two or three times. Alternatively, mesothelial cells are obtained from the homogenates of the cardiac vesicle are washed with PBS and centrifuged at 1,200 rpm for 5 minutes, and then the pellet is suspended in PBS.

(2) PREPARATION OF MYELOMA CELLS

A mouse-derived established myeloma cell line is used. Suitable examples are the 8-azaguanine resistant mouse (BALB/c-derived) myeloma cell lines P3-X63Ag8-U1 (P3-U1) [Current Topics in Microbiology and Immunology 81, 1–7 (1978)], P3-NSI/1-Ag41 (NS-1) [European J. Immunology, 6, 511–519 (1976)], SP2/0-Ag14 (SP-2) [Nature, 276, 269–270 (1978)], P3-X63-Ag8 653 (653) [J. Immunology, 123, 1548–1550 (1979)] and P3-X63-Ag8 (X63) [Nature, 256, 495–497 (1975)], all of which are commercially available. The passage of these cell lines is performed in 8-azaguanine medium [normal medium prepared by adding, to RPMI-1640 medium, glutamine (1.5 mM), 2-mercaptoethanol ($5 \times 10^{-5}$M), gentamicin (10 $\mu$g/ml) and fetal calf serum (FCS; product of CSL) (10%), with further supplementation with 8-azaguanine (15 $\mu$g/ml)]. The cell line selected for cell fusion should be transferred to normal medium 3 to 4 days before fusion to ensure the cell count of not less than $2 \times 10^7$ on the day of fusion.

(3) CELL FUSION

The antibody-producing cells immunized in (1) and the myeloma cells obtained in (2) are washed well with MEM or PBS and mixed in a cell number ratio of antibody-producing cells:myeloma cells in the range of 5:1 to 10:1 and then subjected to centrifugation (1,200 rpm, 5 minutes). The supernatant is discarded and the cell sediment is loosened up. With stirring at 37° C., a mixture of 2 g of polyethylene glycol 1,000 (PEG-1,000), 2 ml of MEM and 0.7 ml of dimethylsulfoxide is added in an amount of 0.2–1 ml per $10^3$ antibody-producing cells, and MEM is added until the whole volume is made 50 ml after several additions of 1–2 ml of MEM at 1 to 2 minute intervals. After centrifugation (900 rpm, 5 minutes), the supernatant is discarded and the cell sediment is loosened gently. To the cells is added 100 ml of normal medium (RPMI-1640 with 10% FCS). The cells are gently suspended in the medium with a measuring pipette.

The suspension obtained is distributed, in 1 ml-portions, into the wells of a 24-well incubation plate. Incubation is carried out in a 5% $CO_2$ incubator at 37° C. for 24 hours. HAT medium [normal medium supplemented with hypoxanthine ($10^{-4}$M), thymidine ($1.5 \times 10^{-5}$M) and aminopterine ($4 \times 10^{-7}$M] is added to the incubation plate (1 ml per well) and incubation is conducted for a further 24 hours. Thereafter, 1 ml of the culture supernatant is discarded and the same volume of fresh HAT medium is added at 24-hour intervals for 2 days. The incubation in the $CO_2$ incubator at 37° C. is continued for 10–14 days.

In those wells in which grown fused colony-forming cells are found, 1 ml of the supernatant is discarded and the same volume of HT medium (HAT medium minus aminopterine) is added, followed by medium replacement with fresh portions of HT medium at 24-hour intervals for 2 days.

After 3 to 4 days of cultivation in HT medium, a portion of the culture supernatant is collected and assayed for antibody titer relative to human mesothelial cells by the above-mentioned immunocytochemical staining. In like manner, the reactivities with normal human cells or tumor cells are also determined, and those wells in which selective reactivity with human mesothelial cells are selected.

Cloning is repeated twice by limiting dilution technique and those clones for which high antibody titer value are stably obtainable relative to human mesothelial cells, are selected as anti-human mesothelial cell monoclonal antibody-producing hybridoma cell lines.

(4) PREPARATION OF MONOCLONAL ANTIBODY

Eight- to ten-week-old female BALB/c mice treated with pristine [intraperitoneally administered with 0.5 ml of 2, 6, 10, 14-tetramethylpentadecane (pristane) and fed for 2-weeks] are intraperitoneally injected with the anti-human mesothelial cell monoclonal antibody-producing hybridoma cells obtained in procedure (3) above at a dose of $2-4 \times 10^6$ cells per animal. In 10–21 days, the hybridoma cells produce ascites carcinoma in the mice. The ascitic fluid is collected from such mice, centrifuged (3,000 rpm, 5 minutes) to remove solids, subjected to salting out with 50% ammonium sulfate, dialyzed against 0.04M phosphate buffer (pH 8.0) supplemented with 0.03M NaCl, and passed through DE52 ® (product of Whatman) column. An IgG fraction is collected and used as a purified monoclonal antibody.

The isotype of the antibody is determined by Ouchterlony's method (double immunodiffusion) [Seibutsukagaku Jikkenho (Methods in Experimental Biochemistry), vol. 15, Introduction to Experimental Immunology, p. 74, Gakkai Shuppan Center, 1981].

The quality of protein is estimated by the Folin's method, followed by calculation based on the absorbance at 280 nm [1.4 ($OD_{280}$) approximately corresponds to 1 mg of immunoglobulin per ml].

The monoclonal antibody thus obtained is effective in cytological diagnosis of expectoration for lung cancer and cytological diagnosis of pleural effusion for lung cancer and cytological diagnosis of ascitic fluid for various abdominal cancers by the above-mentioned immunocytochemical staining.

Certain specific embodiments of the present invention are illustrated by the following examples.

EXAMPLE 1

(1) PREPARATION OF ANTIBODY-PRODUCING CELLS

Eight-week old female BALB/c mice (Shizuoka Agricultural Cooperative Association for Laboratory Animals) were intraperitoneally administered and immunised with human mesothelial cells ($2 \times 10^6$ cells per animal) as an antigen, together with aluminium hydroxide gel (2 mg per animal) and killed B. pertussis vaccine (Chiba Serum Institute; $1 \times 10^9$ cells per animal) as an adjuvant. The same antigen administration was repeated 3–5 times at a dose of $2\times 10^6$ cells per animal at 1 to 2 week intervals without an adjuvant. From among these immunized mice, those mice whose antisera intensely reacted with human mesothelial cells were selected, and spleen cells were prepared from such mice and submitted to cell fusion.

(2) PREPARATION OF MYELOMA CELLS

The 8-azaguanine-resistant murine myeloma cell line P3-U1 was cultivated in normal medium to thereby secure not less than $2\times 10^7$ cells at the time of cell fusion, and submitted to cell fusion as a parent strain.

(3) HYBRIDOMA PRODUCTION

The spleen cells and myeloma cells obtained in (1) and (2), respectively, were used in a ratio of 5:1 and subjected to fusion according to the procedure previously described. After cultivation in HAT medium at 37° C. in 5% $CO_2$ incubator for 14 days, fused cells were selected, and after change of the medium to HT medium, cultivation was continued. Based on the results of anti-human mesothelial cell antibody titer determination, active wells were selected, and after change of the medium to normal medium, cloning was repeated twice by the limiting dilution technique. The clone for which antibody titer value was stably obtainable relative to human mesothelial cells was selected as anti-human mesothelial cell-producing hybridoma cell line KM-277. The hybridoma cell line KM-277 has been deposited with the European Collection of Animal Cell Cultures, Great Britain, as of October 23, 1986 as ECACC No. 86102303 under the Budapest Treaty.

(4) MONOCLONAL ANTIBODY PURIFICATION

Eight-week-old female BALB/c mice treated with pristane were intraperitoneally injected with the hybridoma cell line KM-277 obtained in (3) at a dose of $4\times 10^6$ cells per animal. In 10–21 days, the hybridoma produced ascites carcinoma. The ascitic fluid was collected from ascitic fluid-bearing mice (5 to 10 ml per animal), centrifuged to remove solids (3,000 rpm, 5 minutes), subjected to salting out with 40% ammonium sulfate, dialyzed against 0.04M phosphate buffer supplemented with NaCl (0.03M), and passed through a DE52 ® (product of Whatman) column (bed volume: 50 ml) at a flow rate of 20 to 30 ml/hr. An IgG fraction was collected and used as the purified antibody.

(5) ANTIGENIC SPECIFICITY OF KM-277

The specificity of the thus-obtained monoclonal antibody KM-277 for three human mesothelial cell samples, two human peripheral lymphocyte cell (PBL) samples and various cancer cell lines was investigated using immunocytochemical staining.

The results are shown in Table 1.

TABLE 1

| Sample or Cell line | Staining level by KM-277* |
|---|---|
| Mesothelial cell sample A | ++ |
| B | + |
| C | ++ |
| PBL sample A | − |
| B | ± |
| Myeloma cell line SK-Ly-18 | − |
| T cell leukemia cell lines HSB-2 | − |
| MOLT-3 | − |
| Lung cancer cell line PC-10 | − |
| PC-7 | − |
| PC-13 | − |
| PC-6 | − |
| Gastric cancer cell line MKN-1 | − |
| KATO-III | − |
| Pancreatic cancer cell line HPAF | − |
| Malignant melanoma cell line SK-28 | − |
| Fetal lung cell line L-132 | − |
| Fetal skin cell line Detroit 551 | − |

*Staining level observed with microscope.

As shown in Table 1, KM-277 was very specifically reactive with the human mesothelial cell but not with PBL and the various cancer cell lines.

EXAMPLE 2

In this example, cells in sputum samples and pleural effusion samples derived from three patients with lung cancer, and cells in ascitic fluid samples derived from four patients with gastric cancer were stained by the immunocytochemical staining using KM-277. The mesothelial cells in smeared preparations (smear) were stained and cancer cells in all the preparations were not stained. Therefore, cancer cells can be distinguished from mesothelial cells in smears.

What is claimed is:

1. An anti-human mesothelial cell monoclonal antibody, which is produced from hybridoma cell line KM-277, ECACC No. 86102303, belongs to the class IgG and reacts with human mesothelial cell but not with other normal human cells and human tumor cells.

2. The hybridoma cell line KM-277, ECACC No. 86102303.

3. An immunocytochemical staining method for distinguishing human tumor cells from human mesothelial cells in samples from patients suspected of having tumors, which comprises applying to the samples a monoclonal antibody as defined in claim 1, staining the thus-treated samples to determine the selective reaction of the antibody with human mesothelial cells and the absence of a reaction with human tumor cells, and observing the stained sample.

* * * * *